United States Patent [19]

Geiser

[11] Patent Number: 4,682,374

[45] Date of Patent: Jul. 28, 1987

[54] PROTECTIVE EAR COVERING

[76] Inventor: Joseph Geiser, P.O. Box J, Pocono Lake, Pa. 18347

[21] Appl. No.: 838,479

[22] Filed: Mar. 5, 1986

[51] Int. Cl.$^4$ ............................................ A41D 21/00
[52] U.S. Cl. .......................................... 2/209; 2/423; 2/449; 2/DIG. 6; 351/123
[58] Field of Search .................. 2/209, 171, 170, 423, 2/422, 185 R, 199, 448, 449, 426, 174, DIG. 6; 351/123

[56] References Cited

U.S. PATENT DOCUMENTS

| | | | |
|---|---|---|---|
| 2,241,736 | 5/1941 | Reinemer | 2/209 |
| 2,333,392 | 11/1943 | Rosenzweig | 2/209 |
| 2,593,892 | 4/1952 | Kindel | 2/209 X |
| 2,886,818 | 5/1959 | Roberts | 2/209 X |
| 3,235,882 | 2/1966 | Coleman | 2/174 |
| 3,845,505 | 11/1974 | Davison et al. | 2/209 |
| 4,236,658 | 12/1980 | Kallman | 2/DIG. 6 X |
| 4,404,434 | 9/1983 | Pelt et al. | 2/209 X |

FOREIGN PATENT DOCUMENTS

| | | | |
|---|---|---|---|
| 2280097 | 2/1976 | France | 351/123 |
| 0200837 | 1/1939 | Switzerland | 2/209 |

*Primary Examiner*—Peter Nerbun
*Attorney, Agent, or Firm*—Ruth Moyerman

[57] ABSTRACT

A protective ear covering has a self-fastening strap to fasten to the goggle strap of ski goggles or to a fabric headband. The ear protector's outer edge includes wedge-shaped riser to accommodate an ear's outward projection, while the inside rim of the protector, circumscribed by a deformable gasket, rests flat against a wearer's head. There is preferably an inner liner for warmth and comfort, and vents for ventilation and sound penetration are provided.

6 Claims, 5 Drawing Figures

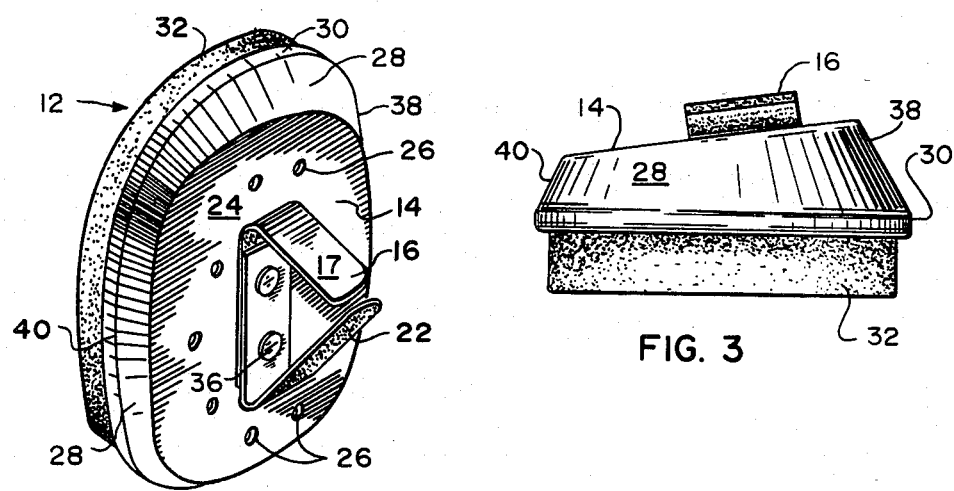
FIG. 2
FIG. 3
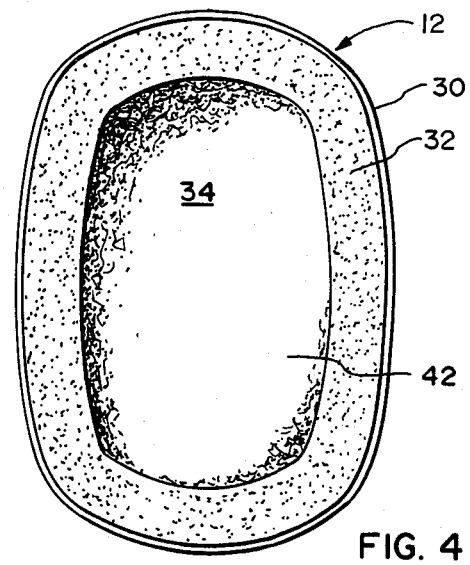
FIG. 4
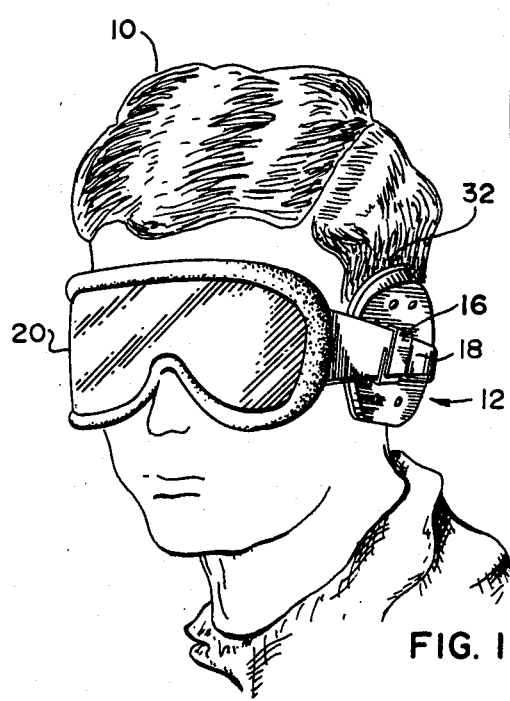
FIG. 1

4,682,374

PROTECTIVE EAR COVERING

BACKGROUND OF THE INVENTION

1. Field of the Invention

This invention relates to apparel and more particularly to ear coverings.

2. Background of the Invention

There are various ear covering devices known in the art. Most relate either to warmth (as the simple fabric or fur ear muffs worn by children) or to protection from the damaging effects of loud sounds, such as those ear protectors worn by airport workers.

Of those intended to protect or warm the ears are U.S. Pat. No. Des. 276,855 to Falco; U.S. Pat. No. 3,943,574 to Yamaguchi and U.S. Pat. No. 3,796,855 to Brown. Falco's design in an earmuff cup, bevelled on its exterior to provide a cup into which an earmuff could be placed. It protrudes from the head, forming its highest point at its midpoint. Yamaguchi shows a ski mask which includes bowl-shaped ear protectors on which the ski mask rests. The ear bowls are joined by an overhead strap and serve to hold the face mask to the head. Brown disclosed ear heating pads which are connected by wiring to either house current or portable battery pack.

None of the prior art shows ear protectors which include means to fasten to ski goggles or fabric headbands worn around the head from forehead to the back of the head and which are shaped to closely surround the ear while affording protection from the cold and allowing adequate sound penetration for safety.

SUMMARY OF THE DISCLOSURE

The prior art problems are obviated by the ear protectors of this invention which preferably are constructed to enable them to be fastened to goggle straps or temple pieces of ski goggles or to fabric headbands. The ear protectors have a generally rounded case which includes a hollow inner section to accommodate an ear. The inner section is preferably lined with a heat retaining fabric.

The case has a generally eliptical, wedge-shaped, riser which, because of the wedge, raises the case portion which rests behind a wearer's ear. The inner surface of the case is flat and includes a preferably deformable, circumferential gasket to provide a close and comfortable fit to the head. Attached centrally to the outside of the case is, preferably, a strap which loops around the goggle strap of ski goggles or around a fabric headband. Also, preferably, vents are provided to afford ventilation and allow sound to penetrate.

It is therefore an object of this invention to provide an ear protector which fastens to the goggle strap or temple piece of conventional ski goggles.

It is also an object of this invention to provide an ear protector which fastens to a fabric headband, such as a an elastic sweatband or a bandanna.

It is another object of this invention to provide an ear covering with adjustable fastening.

It is still another object of this invention to provide a wedge-shaped case to provide a more comfortable design by allowing for the ear's normal outward projection.

It is yet another object of this invention to provide a rigidly capped ear protector with a soft liner.

It is a further object of this invention to provide an ear protector with vents for circulation and sound penetration.

It is yet a further object of this invention to provide an ear protector which includes a deformable gasket to give close and comfortable fit to the head.

These and other objects will be more readily ascertainable to one skilled in the art from a consideration of the following Figures, description and exemplary embodiments.

BRIEF DESCRIPTION OF THE DRAWING(S)

FIG. 1 illustrates the ear protector of this invention fastened to a pair of ski goggles.

FIG. 2 is an isometric view of the ear protector case with vent holes and attachment strap shown.

FIG. 3 is an end view of the protector showing the wedge-shaped riser.

FIG. 4 shows the inside of the ear protector.

DETAILED DESCRIPTION OF THE PREFERRED EMBODIMENT(S)

Figure 5:
FIG. 5 shows the ear protector of this invention attached to a fabric headband.

Referring now to the drawings and more particularly to FIG. 1, ear protector 12 is seen attached to ski goggles 20 being worn by user 10 (ear protector 12 is naturally intended to be used as a pair). Ear protector 12 is preferably eliptical with bevelled edges and sized to closely overfit the ear of user 10. Ear protector 12 is held tightly to the head by ski goggle temple piece 18. Although FIG. 1 shows ski goggle 20 with rigid temple piece 18, temple piece 18 is intended to include goggle straps and fabric headbands, such as elastic "sweat bands," or bandannas. Some ski goggles on the market have rigid temple pieces 18 joined at their ends by an elastic strap to prevent movement or loss during skiing. Most ski goggles now have an elastic strap which extends completely around the head from one goggle side to the other. In any case, ear protector(s) 12 are held firmly over the ear by wrapping strap 16 around temple piece/goggle strap 18.

When using the ear protector of this invention, the ears are continually kept warm. Goggles can be worn with ski caps. but often are uncomfortable, the temple pieces pressed onto the ears. The unmoving ear protectors 12 with their preferably deformable gasket 32 are comfortable and shaped to contain the ear, not press against it.

Now referring to FIGS. 2 and 3, the preferred embodiment of ear protector 12 is pictured. Case 14 has riser 28, riser edge 30, flat top 24 and vents 26. Gasket 32 is seen surrounding the inner edge of case 14. Strap 16 is fastened to the center of top 24 by fasteners 36.

The wedge shaping of riser 28 is evident in FIG. 2 and especially in FIG. 3. In order to provide a comfortable fit over a user's ear, riser 28 is higher at back edge 38 of ear protector 12 (where protector 12 touches a user's head behind his ear) than it is at the front edge 40 of ear protector 12 where it touches in front of a user's ear. This shaping accommodates for the natural protrusion of an ear. Thus, ear protector 12 fits closely all around the ear while still being comfortable and not pressing down on the ear.

Also shown especially in FIG. 2 is self fastening strap 16. It is preferred that strap 16 have a plain surface 17 backed by a fastening (such as Velcro) surface 22. In use, strap 16 is wrapped around a goggle strap or temple piece 18 (as seen in FIGS. 1 and 5) and the fastening surfaces 22 are pressed against each other to tightly, but unmovably, hold ear protector 12 to temple piece 18. Because strap 16 can be fastened anywhere along its fastening surface, it is adjustable for goggles with temple pieces of varying widths or with goggles employing goggle straps..

Vents 26, seen in FIG. 2, are preferred, although optional. Since protector 12 is held so tightly to the head by goggles 20, sound as well s cold might not penetrate. Vents 26 allow more sound to penetrate so that the skier is able to be warned of dangers as well as being able to converse with fellow skiers. The number and location of vents 26 are optional.

Now referring to FIG. 4, the inside of ear protector 12 is shown. Riser edge 30 is seen circumscribed by gasket 32. Hollow interior 42 is seen lined with heat retaining material 34. For the comfort of the user, it is preferred that a liner be used and that liner 34 be fur or a man-made pile fabric which retains heat as well as being soft against the ear. Gasket 32 is preferably deformable plastic such as polyester foam which is well known in the art to provide for a close fit around the ear, deforming to account for differing head shapes and hairlines. Also, by being deformable, gasket 32 absorbs the pressure of temple piece 18, adding to the comfort of ear protector 12. Gasket 32 may be of various thicknesses and still be effective and comfortable.

Now referring to FIG. 5, user 10 is seen wearing ear protector 12 held over the ears by head band 44. Head band 44 is seen as an elastic head band or "sweat band" as commonly used by athletes. Head band 44 may also be a bandanna tied around the forehead and back of the head. Head band 44 is preferable for use by those skiers who prefer not to wear goggles.

There are several variations possible with ear protector 12. For example, first, liner 34 is optional and any material which conforms to inner area 42 is within the scope of this invention.

Second, case 14 is shown as molded plastic and gasket 32 as polyester foam. However, although these are the preferred materials of construction, any material which performs the same function is intended to be within the scope of this invention. Also, gasket and case, and even the strap, may be made together.

Strap 16 is preferred, but any fastening means which will hold protector 12 onto an extraneous support is within the scope of this invention.

Vents 26, optional in number and location, have been discussed as useful for sound and air filtration. They may also be used for additional attachments, such as radio speakers or microphones.

Also, riser 28 has been shown throughout with riser edge 30. Edge 30 may be eliminated to provide streamlined design and still be within the scope of this invention.

There are many advantages to the ear protector of this invention. Chiefly, it is adaptable to virtually any set of ski goggles or fabric headbands. Second, its wedge shaping makes it comfortable, yet keeps it smoothly shaped for appearance. Third, its liner and construction make use of the body's natural heat to keep the ears warm.

Having now illustrated and described my invention, it is not my intention that such description limit the invention, but that the invention be limited only by a reasonable interpretation of the appended Claims.

What is claimed is:

1. A protective ear covering intended to be worn as a pair in combination with the goggle strap of conventional ski goggles, said ear protector comprising:
   (a) a case sized to overfit a wearer's ear, said case being generally elliptical in longitudinal cross section and including a hollow inner portion to overfit a wearer's ear, said case including a wedge-shaped riser and a flattened top, said top thereby forming generally an inclined plane with said riser to cause said case portion touching the user's head behind the ear to rise to accommodate the ear'outward projection;
   (b) a deformable gasket circumscribing said case's inner edge and extending outward therefrom;
   (c) at least one vent extending through said case to provide ventilation and to allow sound to penetrate; and,
   (d) a self-fastening, adjustable attachment strap, said attachment strap sized to at least surround the width of said goggle strap and attached to said case top exterior proximate its midpoint.

2. The protective ear covering according to claim 1. including, additionally, a heat retaining liner sized to cover said case's interior hollow portion.

3. The protective ear covering according to claim 1 wherein said case is made of flexible polyethylene.

4. The protective ear covering according to claim 1 wherein said deformable circumferential gasket is polyester foam.

5. A protective ear covering intended to be worn as a pair comprising:
   (a) a case sized to overfit a user's ear, said case being generally elliptical in longitudinal cross section and including a hollow inner portion to overfit a wearer's ear, said case including a wedge-shaped riser and a flattened top, said top thereby forming an inclined plane with said riser to cause said case portion touching the user's head behind the ear to rise to accommodate the ear's outward projection;
   (b) a deformable gasket circumscribing said case's inner edge and extending outward therefrom;
   (c) at least one vent extending through said case to provide ventilation and to allow sound to penetrate;
   (d) a fabric headband
   (e) an adjustable, self fastening attachment strap, said attachment strap sized to at least surround the width of said fabric headband, said attachment strap attached to said case top exterior proximate its midpoint, and;
   so that when said protective ear covering is placed over a wearer's ears, said attachment strap surrounds said fabric headband to hold said protective ear covering to a wearer's ear.

6. The protective ear covering according to claim 5 including, additionally, a heat retaining liner sized to cover said case's interior hollow portion.

* * * * *